US007778458B2

(12) United States Patent
Hiraoka

(10) Patent No.: US 7,778,458 B2
(45) Date of Patent: Aug. 17, 2010

(54) METHOD, APPARATUS AND PROGRAM PRODUCT FOR SEARCHING KNOTS IN WOOD

(75) Inventor: Noriyuki Hiraoka, Obu (JP)

(73) Assignee: Meinan Machinery Works, Inc., Aichi (JP)

( * ) Notice: Subject to any disclaimer, the term of this patent is extended or adjusted under 35 U.S.C. 154(b) by 1128 days.

(21) Appl. No.: 11/383,631

(22) Filed: May 16, 2006

(65) Prior Publication Data
US 2006/0262972 A1 Nov. 23, 2006

(30) Foreign Application Priority Data
May 18, 2005 (JP) ............................. 2005-145146

(51) Int. Cl.
*G06K 9/00* (2006.01)
(52) U.S. Cl. ..................... 382/141; 382/149; 382/159
(58) Field of Classification Search .................. 382/110
See application file for complete search history.

(56) References Cited

U.S. PATENT DOCUMENTS

| 4,907,156 A | * | 3/1990 | Doi et al. ..................... 382/130 |
| 5,544,256 A | * | 8/1996 | Brecher et al. ............... 382/149 |
| 6,922,482 B1 | * | 7/2005 | Ben-Porath ................. 382/149 |
| 7,406,190 B2 | * | 7/2008 | Carman et al. .............. 382/141 |

FOREIGN PATENT DOCUMENTS

| JP | 8145914 | 6/1996 |
| JP | 09-210785 | 8/1997 |

OTHER PUBLICATIONS

JP, Hirokazu Osaki et al., "The Development of CAD for the Sawing of Timber (1st Report, The Method of Recognizing Knots Using the Image Processing Technique", Collected Papers on Japan Society of Mechanical Engineering, 1987, vol. 53, No. 490, pp. 1291-1296.
JP, Fujio Kobayashi, et al., "An Algorithm for Inspecting Defects in Woods", 1993, vol. 22, No. 4, pp. 368-375.

* cited by examiner

*Primary Examiner*—Samir A. Ahmed
*Assistant Examiner*—Ruiping Li
(74) *Attorney, Agent, or Firm*—McGlew and Tuttle, P.C.

(57) ABSTRACT

The photographing means of the present apparatus photographs a piece of wood, while the image processing means calculates degrees of circularity from the photographed images of the piece of wood, and detects images with significant degrees of circularity as knots. In addition, the image processing means 1 clips a portion including a knot from the photographed image of the piece of wood, deems a portion clipped at a predetermined threshold among the color spaces of each pixel of the clipped portions to be a blackened portion, and determines black portions with a high proportion of a number of pixels of the blackened portion to the number of pixels of the clipped portion of the knot as dead knots.

16 Claims, 11 Drawing Sheets

CURVE a

THRESHOLD LEVEL

LARGE DEGREE OF CIRCULARITY: LARGE INTEGRATED VALUE

SMALL DEGREE OF CIRCULARITY: SMALL INTEGRATED VALUE

FIG. 7A
FIG. 7B
RESULTING IMAGE
(KNOT PORTIONS ARE EMPHASIZED)
BINARIZED IMAGE
(KNOT CANDIDATES)
 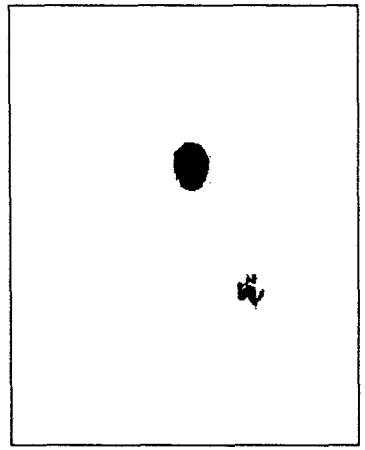

DEGREE OF CIRCULARITY
INTEGRATION IMAGE

DIFFERENTIAL
IMAGE

KNOT CANDIDATE OBTAINED
BY DEGREE OF CIRCULARITY
INTEGRATION

BINARIZED BY
OPTIMAL
THRESHOLD

METHOD, APPARATUS AND PROGRAM PRODUCT FOR SEARCHING KNOTS IN WOOD

CROSS-REFERENCE TO RELATED APPLICATIONS

This application claims priority from Japanese patent application Serial no. 2005-145146 filed May 18, 2005, the contents of which are incorporated by reference herein.

BACKGROUND OF THE INVENTION

1. Field of the Invention

The present invention relates to a method, an apparatus and a program product for searching knots in wood-based material such as veneers or cut pieces cut from logs of wood or the like. For example, for manufacturing plywood, a log is cut using a cutting tool to consecutively obtain veneers with a thickness of several millimeters. The veneers are then cut to a predetermined size, and after drying, several veneers are integrated through lamination using an adhesive. During such manufacturing processes, it is necessary to sort (for instance, into five to seven grades) the veneers into those that will compose the outer layers of plywood, and those that will compose the inner layers according to degrees of positions, numbers and dimensions or the like of knots, unsound knots that have fallen out, cracks, and other defects such as discoloration due to mold or pitch that are found on the veneers. In other words, veneers are sorted to those with little or no aesthetic defects to be used as outer layers, and those that will comprise inner layers where such aesthetic defects, even if they exist in abundance, are irrelevant.

Conventionally, the process of sorting boards into those to be used as outer layers of plywood and those to be used as inner layers thereof has involved naked eye determination by a worker on veneers conveyed through a conveyer.

In addition, an example of a conventional method for automatically detecting defects in wood is described in Patent Document 1, wherein imperfections such as knots, cracks, rot and the like on the surfaces of wood to be laminated were detected using a linear television camera. This defect detection method involved determining defects to be removed based on whether color shading and the like of a detected surface exceed certain comparative judgment data.

Patent Document 1: Japanese Patent Laid-Open 8-145914

2. Description of the Related Art

The above-described conventional method had the following problems.

Naked eye determination led to inconsistencies from person to person (inaccuracy), and did not allow conveyor speed to be increased (low productivity).

In addition, since determination of defects using a linear television camera was solely based on color shading, there was a problem where configuration of knots, defects and the like could not be accurately detected.

SUMMARY OF THE INVENTION

An object of the present invention is to be capable of accurately detecting of configuration of knots, defective knots or the like.

(1) The present invention is a method for searching knots in wood, wherein: a piece of wood is photographed by photographing means; degrees of circularity are calculated from each figure of the photographed images of the piece of wood; and one or more images of figures with significant degrees of circularity are detected as knots. Therefore, accurate detection of knots in wood may be achieved.

(2) In addition, the present invention is a method for searching knots in wood, wherein: a piece of wood is photographed by photographing means; degrees of circularity are calculated from the photographed images of the piece of wood; an image of figure with a significant degree of circularity is deemed a knot candidate; at least a partial image including the knot candidate is clipped from the photographed image of the piece of wood; color shading threshold levels are varied for the clipped partial image to obtain a threshold level where the degree of circularity and size stability are both maximum, and a knot configuration is determined. Therefore, accurate determination of knot configurations in wood may be achieved.

(3) Moreover, according to the method for searching knots in wood described in above (2), the present invention varies the color shading threshold levels of the photographed images of the piece of wood to obtain degrees of circularity of each image; multiplies the image of each threshold level by coefficients derived from the obtained degrees of circularity; integrates the images respectively calculated for each threshold level and deems the integrated image to be a knot candidate. Therefore, accurate detection of knot candidates in wood may be achieved.

(4) According to the method for searching knots in wood described in above (2) or (3), the present invention performs smoothing of color shadings that are larger than knots on the photographed images of the piece of wood; calculates degrees of circularity on the smoothed images; and deems the images with high degrees of circularity to be knot candidates. Therefore, accurate and prompt detection of knot candidates in wood may be achieved.

(5) The present invention is a method for searching knots in wood, wherein: a piece of wood is photographed by photographing means; degrees of circularity are calculated from each figure of the photographed images of the piece of wood; an image of figure with a significant degree of circularity is deemed to be a knot candidate; at least a partial image including the knot candidate is clipped from the photographed image of the piece of wood; a partial image clipped at a predetermined threshold among the color spaces of each pixel of the clipped partial image is deemed to be a blackened portion; and black portions with a high proportion of a number of pixels of the blackened portion to the number of pixels of the knot candidate is determined as a dead knot. Therefore, accurate detection of dead knots with bark in wood may be achieved.

Furthermore, the present invention is an apparatus for performing the above processing, or a program product for having a computer execute the above processing.

The present invention has the following advantageous effects.

(1) Since a piece of wood is photographed by photographing means; and image processing means calculates degrees of circularity from the photographed images of the piece of wood and detects images with significant degrees of circularity as knots, accurate detection of knots in wood may be achieved.

(2) Since a piece of wood is photographed by photographing means; and image processing means calculates degrees of circularity from the photographed images of the piece of wood, deems an image with a significant degree of circularity to be a knot candidate, clips at least a portion including the knot candidate from the photographed image of the piece of wood, and varies color shading threshold levels for the clipped image to obtain a threshold level where the degree of circularity and size stability are both maximum to determine knot configuration, accurate determination of knot configurations in wood may be achieved.

(3) Since the image processing means varies the color shading threshold levels of the photographed images of the piece of wood to obtain degrees of circularity of each image; multiplies the image of each threshold level by coefficients derived from the obtained degrees of circularity; integrates the images respectively calculated for each threshold level; and deems the integrated image to be the knot candidate, accurate detection of knot candidates in wood may be achieved.

(4) Since the image processing means performs smoothing on color shadings that are larger than knots on the photographed images of the piece of wood; calculates degrees of circularity on the smoothed images; and deems an image with a high degree of circularity to be a knot candidate, accurate and prompt detection of knot candidates in wood may be achieved.

(5) Since the image processing means clips at least a portion including the knot candidate from the photographed images of the piece of wood; deems a portion clipped at a predetermined threshold among the color spaces of each pixel of the clipped portions to be a blackened portion; and determines black portions with a high proportion of a number of pixels of the blackened portion to the number of pixels of the knot candidate as dead knots, accurate detection of dead knots with bark in wood may be achieved.

BRIEF DESCRIPTION OF THE DRAWINGS

FIGS. 7A and 7B are explanatory diagrams of an integration result according to the present invention;

DETAILED DESCRIPTION OF THE PREFERRED EMBODIMENTS (1) Description of the Veneer Sorting Apparatus FIG. 1 is an explanatory diagram of the veneer sorting apparatus, which depicts an overall configuration of the veneer sorting apparatus.

Figure 1:
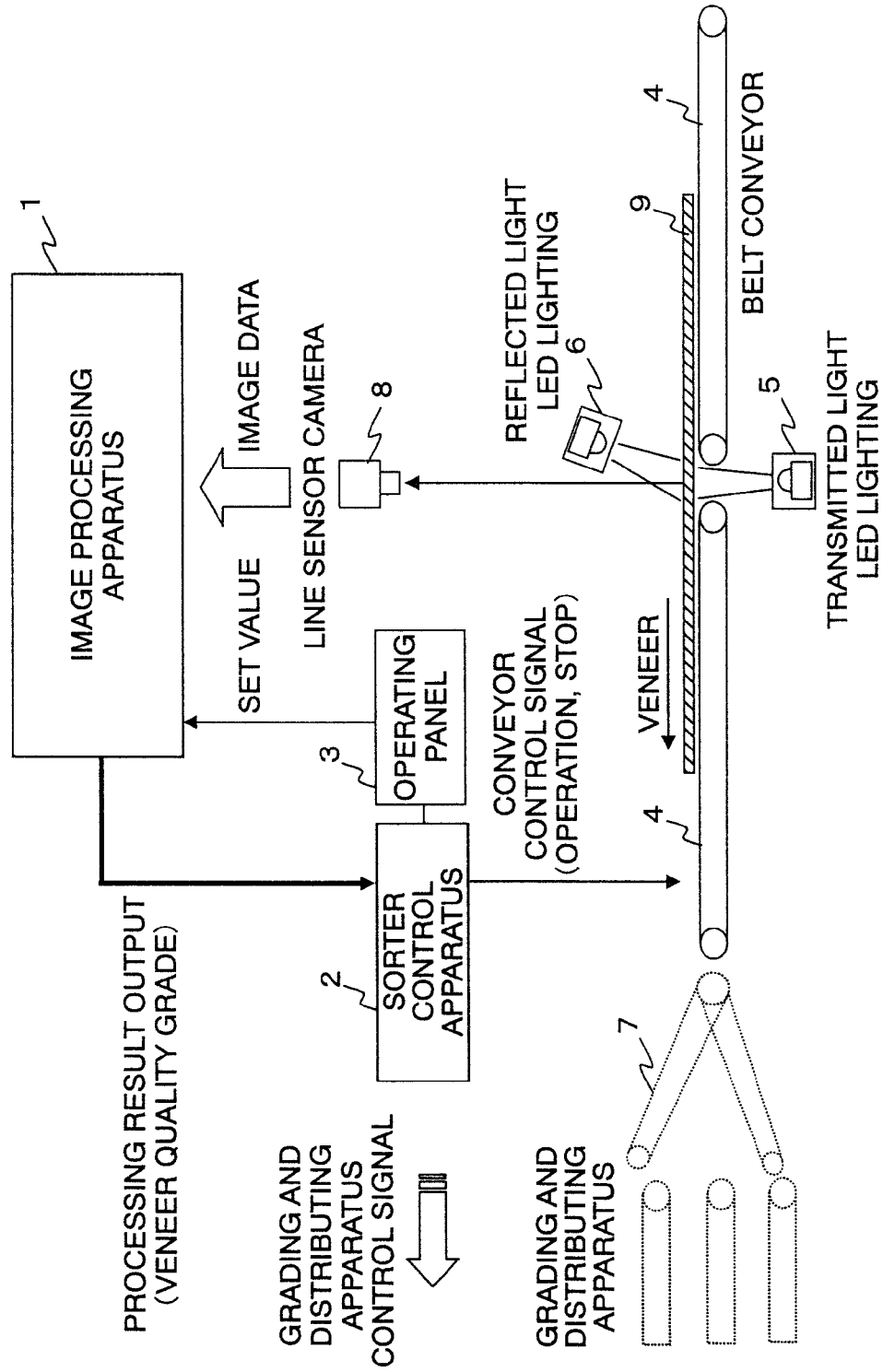
FIG. 1 is an explanatory diagram of a veneer sorting apparatus according to the present invention.

The veneer sorting apparatus of FIG. 1 includes an image processing apparatus 1, a sorter control apparatus 2, an operating panel 3, a belt conveyor 4, a transmitted light LED lighting 5, a reflected light LED lighting 6, a grading and distributing apparatus 7, a line sensor camera 8, and a veneer 9.

The image processing apparatus 1 is processing means that processes image data from the line sensor camera 8, and outputs processing results such as veneer quality grading to the sorter control apparatus 2.

The sorter control apparatus 2 is processing means that outputs sorter conveyor control signals such as for operating and stopping the conveyor, and control signals for the grading and distributing apparatus 7 in response to output from the image processing apparatus 1.

The operating panel 3 is a panel for performing operations such as changing the set values of the image processing apparatus 1, and controlling of the sorter control apparatus 2.

The belt conveyor 4 is conveying means for conveying the veneer 9.

The transmitted light LED lighting 5 is lighting means for detecting holes in the veneer 9, and uses lighting such as green lighting which differs in color from the reflected light LED lighting 6. Lighting from the transmitted light LED lighting 5 is differentiated from the reflected light from the reflected light LED lighting 6 in both color and intensity to detect holes (knot holes), cracks or the like in veneers.

The reflected light LED lighting 6 is lighting means for detecting light reflecting off the veneer 9, and normally is a white lighting.

The line sensor camera 8 is photographing means for taking line images of the veneer 9.

In operation of the veneer sorting apparatus, the line sensor camera 8 photographs the veneer 9 conveyed by the belt conveyor 4, and outputs the image data to the image processing apparatus 1. The image processing apparatus 1 processes the image data, and outputs processing results such as veneer quality grade to the sorter control apparatus 2. The sorter control apparatus 2 outputs a control signal to the grading and distributing apparatus 7 to sort the veneer 9 according to grades. Sorting is performed according to the numbers of wormholes, holes or fallen knots, live knots, dead knots, wanes, cracks, pitch and bark pockets, blue stains and the like, as well as their respective sizes (dimensions).

(2) Description of the Image Processing Apparatus

Figure 2:
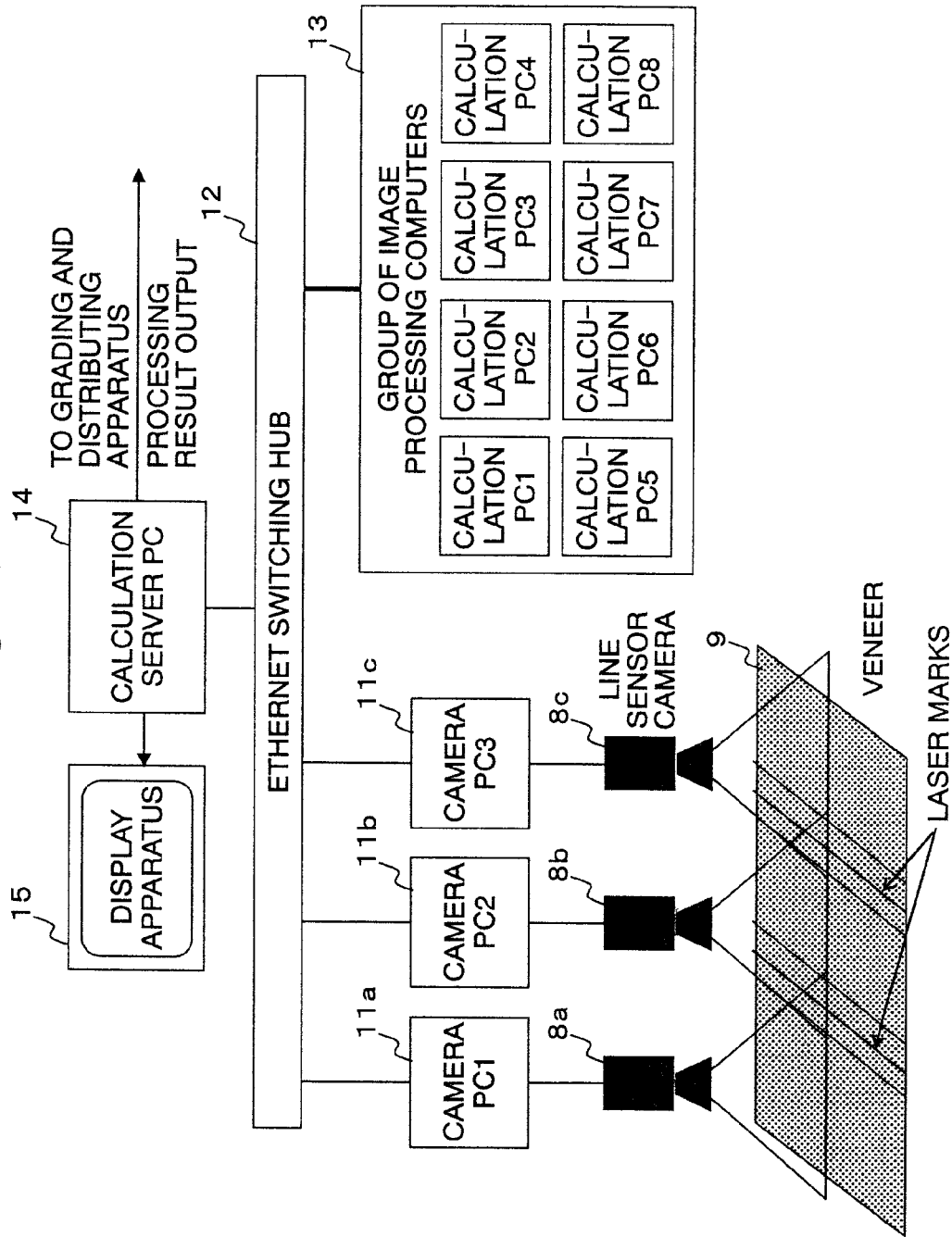
FIG. 2 is an explanatory diagram of an image processing apparatus according to the present invention.

FIG. 2 is an explanatory diagram of the image processing apparatus.

In FIG. 2, the image processing apparatus includes three line sensor cameras 8a, 8b and 8c, a camera computer 11a (shown as a camera PC1), a camera computer 11b (shown as camera PC2), a camera computer 11c (shown as camera PC3), an Ethernet (registered trademark) switching hub (HUB) 12, a group of image processing computers 13, a calculation server computer 14 (shown as a calculation server PC) 14, and a display apparatus 15.

The line sensor cameras 8a, 8b and 8c are photographing means which uses three cameras to photograph the veneer in three equal sections in a direction that is perpendicular to the conveying direction.

The camera computers 11 (camera PC1 to PC3) deliver image data to the group of image processing computers 13 and the calculation server PC 14 via the Ethernet switching hub (HUB) 12 whenever a single line image is loaded from each line sensor camera.

The Ethernet switching hub (HUB) 12 is data relay means for distributing image data from the line sensor cameras 8a, 8b and 8c.

The group of image processing calculators 13 is processing means for processing (knot searching and defect searching processing) grayscale images of the veneer by dividing and sharing the processing among calculation hosts (shown as calculation PC1 to PC8).

While image data is stored in the respective storage means of the calculation computers 13 (calculation PC1 to PC8), processing of the image data is shared.

The calculation server PC 14 forwards processing instructions to each calculation PC of the group of image processing computers 13, and depending on processing results from the group of image processing computers 13, outputs control signals to the grading and distributing apparatus 7 which is a sorter, and also outputs to the display apparatus to display processing results or the like.

The display apparatus 15 is a display apparatus for displaying image processing results or the like.

In operation of the image processing apparatus, the camera PC1 to PC3 deliver image data to the calculation PC1 through PC8 and the calculation server PC 14 whenever a single line image is loaded from the line sensor cameras 8a to 8c. The calculation PC1 to PC8 sequentially join the received images. Eventually, by the time the camera PC1 to PC3 complete loading of images, each calculation PC1 to PC8 has virtually finished color image synthesis and grayscale image conversion.

The tripartitioned veneer images from the camera PC1 to PC3 are joined at the group of image processing computers 13. Each calculation PC1 to PC8 handles an eighth of the processing. This allows effective utilization of loading time.

The veneer 9 is tripartitioned by marks irradiated by a laser marker, not shown. The line sensor cameras 8a, 8b and 8c are arranged so that joining of images can be easily performed by matching line images that end at each laser mark. Additionally, in order to increase image processing speed, knot searching processing can be performed using grayscale images which have large numbers of pixels, while searching processing for dead knots and the like can be performed using scaled-down (with reduced number of pixels) color images.

The operation of the image processing apparatus will now be described in two stages, namely processing during photographing, and processing thereafter.

<Description of Processing During Photographing>

Image data photographed by the line sensor cameras 8a, 8b and 8c is distributed to the calculation server PC 14 and all calculation PC1 to PC8 for each line, and is synthesized as a single overall image at each recipient PC. This enables photographing time to be utilized more efficiently as compared to a method where images are transmitted after completion of shooting.

As processing at the camera PC1 to PC3, single line color images are loaded from the line sensor cameras 8a, 8b and 8c, and laser mark positions as junction locations are detected. Then, along with this information, the single line color images are transmitted to the calculation server PC 14 and all calculation PC1 to PC8.

As processing at the calculation server PC 14 and all calculation PC1 to PC8, the arrived single line color images are synthesized based on the above position information. By the time photographing by the camera PC1 to PC3 has completed and the last single line color image is received, synthesis of an overall color image will be concluded at the calculation server PC 14 and each calculation PC1 to PC8. As seen, since photographing time is efficiently utilized, processing performable for each single line such as black and white conversion and reduction processing may be performed concurrently.

<Description of Processing During Image Analysis Following Photographing>

As processing at the camera PC1 to PC3, the camera PC1 to PC3 await the arrival of the next board (veneer).

As processing at the calculation server PC 14, based on predetermined information such as size and type of the target board, the calculation server PC 14 instructs regions to be calculated and set values to the calculation PC1 to PC8. The calculation server PC 14 itself performs defect detection processing using transmitted light, and receives analysis results from the calculation PC1 to PC8 to eventually perform grading processing. The results thereof are displayed on the display device 15, and are also outputted to the sorter control apparatus.

As processing at the calculation PC1 to PC8, one calculation PC calculates color deviation (within a color space, distance from a color center is normalized to 1.0) of a surface using a scaled-down color image, and detects defects such as blackened portions, blue stains and dead knots from the calculation results. The other calculation PCs, as knot searching calculation PCs, use a grayscale image to search for whichever knot that is most time-consuming. The knot searching calculation PCs divide and share analysis processing according to region based an calculation regions and threshold information distributed from the calculation server PC14. Thus, the number of calculation PCs is determined by the dimensions of the veneer (board) to be measured as well as the time required for outputting results.

While a plurality of computers (PCs) such as the camera PCs, the calculation server PC 14, and the image processing calculators 13 within the image processing apparatus are used in the above description, the number of computers to be used may be changed according to image data volume or processing speeds of computers. Or the processing may even be carried out by a sole computer.

(3) Description of Knot Searching

The items (a) to (e) below can be considered as requirements for knots to be detected.

(a) Generally dark (low lightness);
(b) Darker than its surrounding areas within a partial region (low brightness);
(c) Darkness steeply rises in its boundary portion;
(d) Likely to have a circular configuration; and
(e) Surrounded by a concentric grain.

Areas that have many items that apply can be considered knot candidates. Therefore, by noting that dark portions (with low lightness), which is a characteristic of knots, are usually circular, a probability distribution is calculated for a dark portion to identify a knot candidate. In other words, in the method described in the section titled (B) Description of a method for configuration integration, knot candidates can be determined by binarizing grayscale images while varying threshold levels, and adding a larger value to individual binarized blocks with configurations similar to a circle to perform integration. Moreover, alterations can be made for knot searching depending on the material of wood. For instance, certain items can be given more weight than others, or the number of items can be reduced.

Figure 3:
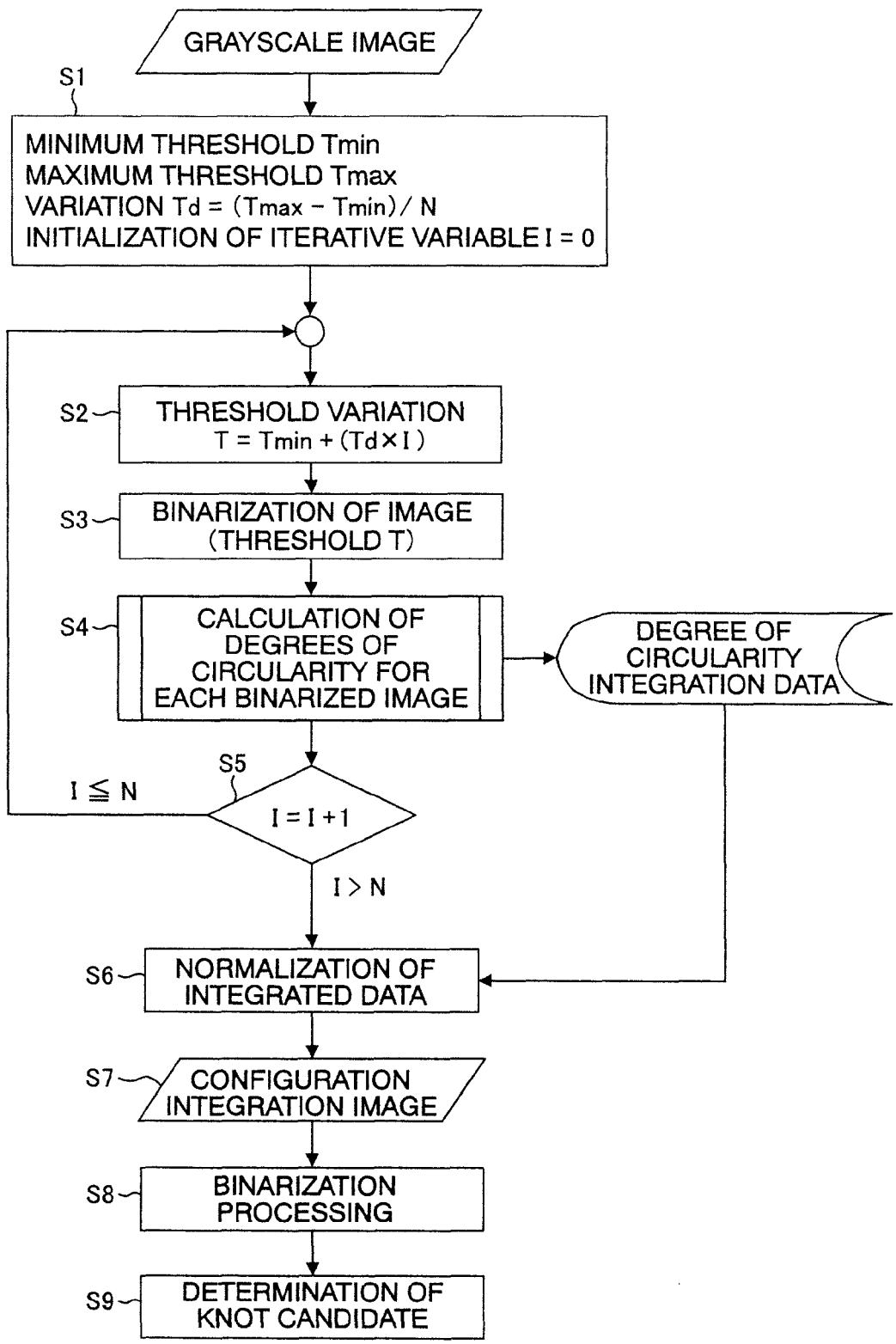
FIG. 3 is a flowchart of knot searching processing according to the present invention.

FIG. 3 is a flowchart of knot searching processing. The following description will follow the processing steps S1 to S9 shown in FIG. 3.

S1: The image processing apparatus 1 initializes a minimum threshold Tmin and a maximum threshold Tmax of the color shading of the received grayscale image, a preset division number N of the threshold level, variation Td=(Tmax−Tmin)/N, and an iterative variable I to 0, and proceeds to step S2.

S2: The image processing apparatus 1 changes the color shading threshold (T=Tmin+(Td×I)), and proceeds to step S3.

S3: The image processing apparatus 1 binarizes the image with the color shading threshold T, and proceeds to step S4.

S4: The image processing apparatus 1 calculates values of degree of circularity for each binarized shape, and creates integrated data for each degree of circularity (in another storage area, weight due to degree of circularity is added to perform integration for each pixel for which the degree of circularity was calculated), and proceeds to step S5.

S5: The image processing apparatus 1 adds 1 (I=I+1) to the iterative variable I. If the iterative variable I is equal to or smaller than N (I≦N), the image processing apparatus 1 returns to step S2, and if the iterative variable I is larger than N (I>N), the image processing apparatus 1 proceeds to step S6.

S6: The image processing apparatus 1 performs normalization on the integrated data of the degrees of circularity, and proceeds to step S7.

S7: The image processing apparatus 1 creates an integrated image of the shape from the normalized integrated data, and proceeds to step S8.

S8: The image processing apparatus 1 binarizes the integrated image of the shape, and proceeds to step S9.

S9: The image processing apparatus 1 determines a knot candidate.

Figure 4A:
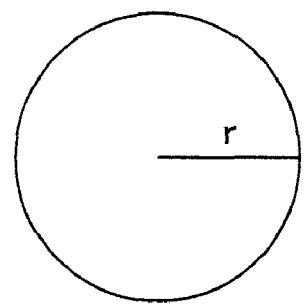
FIGS. 4A and 4B are explanatory diagrams of a method for obtaining a degree of circularity according to the present invention.
Figure 4B:
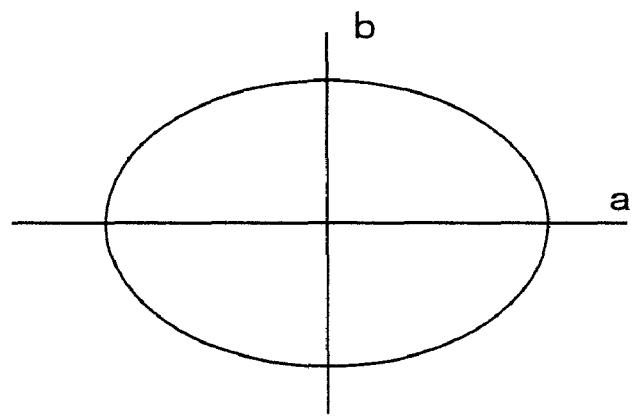

(A) Description of a Method for Calculating Values of Degrees of Circularity for each Binarized Shape Degrees of circularity are obtained as follows. FIGS. 4A and 4B are explanatory diagrams of a method for obtaining degrees of circularity. FIG. 4A describes a circle, while FIG. 4B describes an ellipse. In FIG. 4A, r denotes the radius of the circle. In FIG. 4B, a denotes the semimajor axis, and b denotes the semiminor axis of the ellipse.

In the ellipse diagram of FIG. 4B, the aspect ratio is to be p a/b.

The following are known.
<Circle>
Area: $A=\pi r^2$
Moment of inertia: $I=(\pi/4)r^4$
<Ellipse>
Area: $A=\pi ab$
Moment of inertia: $I=(\pi/4)a^3 \cdot b$
Since the moment of inertia of an ellipse can be written as $$I=(\pi/4)a^3 \cdot b=(1/4\pi)(\pi^2 \cdot a^2 \cdot b^2)(a/b)=(1/4\pi)A^2 \cdot p$$

where p=a/b is the aspect ratio, the formula can be further written as the following formula 1.

$$p=4\pi(I/A^2) \qquad \text{Formula 1}$$

As an actual measurement, the moments of inertia can be written as:

I' (actual measurement)=$\Sigma(x^2+y^2) \cdot g(x,y)$ (sum of squares of the pixel positions for all pixels)

A' (actual measurement)=$\Sigma g(x,y)$ (all pixels)

where the center of the block is the origin, and an image is g (x,y).

Thus, by substituting these into Formula 1, the aspect ratio p can be obtained from the following formula.

$$p=4\pi(I'/A'2)$$

The more flattened an ellipse is, the greater its aspect ratio p. A perfect circle has an aspect ratio p of 1.0. Now, by defining its inverted number 1/p as the degree of circularity, the degree of circularity of an ellipse will vary between 0.0 and 1.0, and the closer the shape is to a circle, the closer the value is to 1.0. Veneers are obtained, for instance, by cutting a log with a blade that is parallel to the longitudinal direction of the log. However, branches exist in the inside of logs at angles that are oblique to a longitudinal direction, which manifest themselves as knots. Therefore, since the configurations of knots are likely to be elliptic rather than circular, areas with degrees of circularity that exceed, for instance 1/8, should be considered knots.

Figure 5:
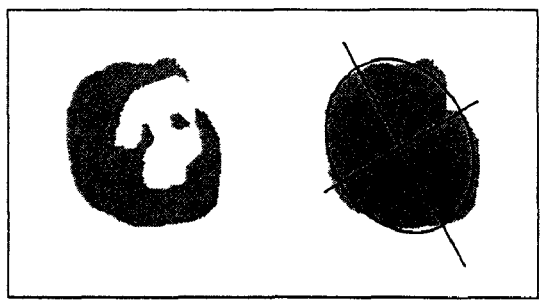
FIG. 5 is an explanatory diagram of a binarized configuration of a knot according to the present invention.

FIG. 5 is an explanatory diagram of a binarized configuration of a knot. As shown in FIG. 5, the binarized configurations of knots do not actually resemble ideal forms as described above, but rather are similar to those shown in the diagram on the left-hand side of FIG. 5. Therefore, a process of filling the inside from an outermost periphery is performed to achieve the condition shown on the right-hand side of FIG. 5. The pseudo-elliptic aspect ratio of the shape is obtained, and is then inverted to arrive at the degree of circularity.

By adding the degrees of circularity obtained in this manner to a memory that uses the coordinates of each pixel of the black block of FIG. 5 as indicators, degree of circularity integration of a pixel binarized by a certain threshold is performed. This allows larger degrees of circularity to be integrated for blocks that are closer to circles.

In addition, by performing the above integration while varying the threshold from minimum to maximum, density and configuration can be studied concurrently.

(B) Description of a Method for Configuration Integration

A density contour line can be obtained by searching the periphery of each block using a grayscale image binarized by a particular threshold. The threshold is changed at regular intervals, and a binarized image for each threshold is integrated individually. An important point is that portions with greater density have values for more thresholds, and enable more contour lines (binarized images) to be obtained (greater integration effect).

Figure 6A:
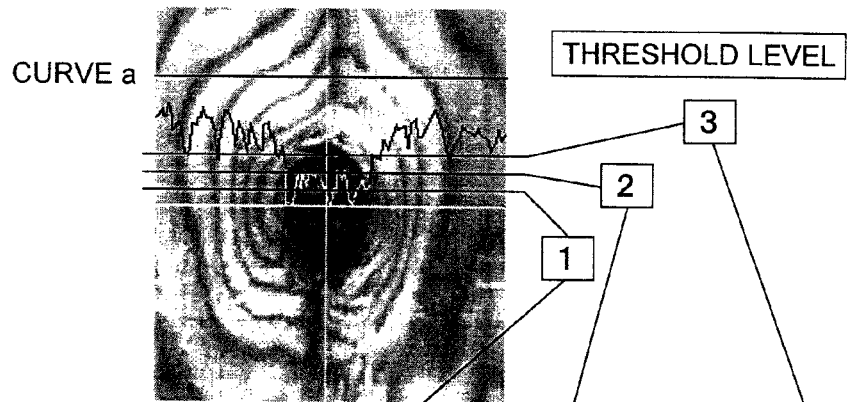
FIGS. 6A, 6B, 6C and 6D are explanatory diagrams of configuration integration according to the present invention.
Figure 6B:
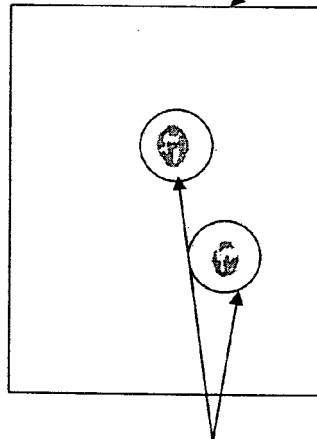
Figure 6C:
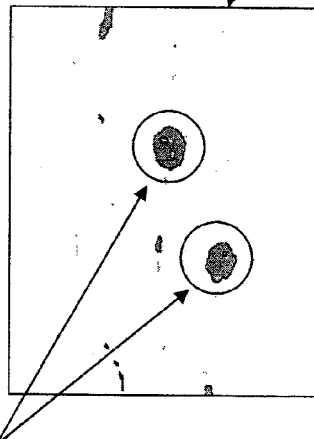
Figure 6D:
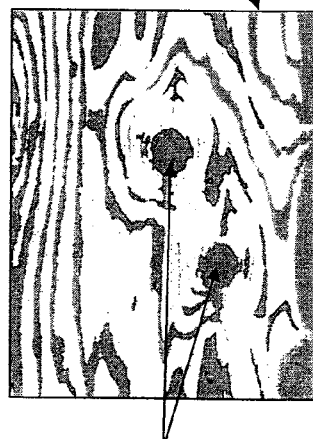

FIGS. 6A, 6B, 6C and 6D are explanatory diagrams of a configuration integration. FIG. 6A illustrates a horizontal density graph, FIG. 6B illustrates an image binarized by threshold level 1, FIG. 6C illustrates an image binarized by threshold level 2, and FIG. 6D illustrates an image binarized by threshold level 3.

FIG. 6A shows a color shading image of an enlarged portion of a knot periphery, and curve a is a density graph of the image in a central horizontal direction (see white horizontal line). With the curve a, upward represents white levels while downward represents black levels, and threshold levels 1, 2 and 3 (black horizontal lines) are indicated.

In FIG. 6B, the image binarized by the threshold level 1 has become an image of only the black portions below threshold level 1, and now has an increased degree of circularity (the circled image). Therefore, large values will be added to each pixel of this image when performing integration. In other words, for each pixel of the image, large values will be added to the memory addresses that correspond to each pixel position.

In FIG. 6C, the image binarized by the threshold level 2 has become an image below threshold level 2, and now has an increased degree of circularity (the circled image). Therefore, this image will have a large integrated value (weighting will be increased and then added).

In FIG. 6D, the image binarized by the threshold level 3 has become an image of only black portions below threshold level 3, where grain patterns have appeared while the degree of circularity has decreased. Therefore, for each pixel of this image, a small positive value or a negative value will be added to the memory addresses that correspond to each pixel position.

FIGS. 7A and 7B are explanatory diagrams of an integration result. FIG. 7A illustrates a result diagram, while FIG. 7B illustrates a binarized image. In FIG. 7A, knot portions will be emphasized in the images of the integration results of the binarized images at each threshold level. In FIG. 7B, knot candidates are obtained by binarizing the image of FIG. 7A. Incidentally, FIG. 7A is an image after black and white inversion.

(C) Description of Smoothing of Irregular Colors using a Local Average Value

The surfaces of veneers are not always monochromatic, and irregular colors often exist. When knots exist (in portions with color shading) in such irregularly colored veneers, the irregular colors must be removed to emphasize only the color shading of the knots. Therefore, the image processing apparatus 1 obtains adjacent average values for each pixel, and corrects light and dark of the original image based on results thereof (processing for detection of knot candidates).

When the original image is f(i,j), and the smoothed image is g(i,j), an average of the vicinity of the image (i,j) can be obtained by $$g(i, j) = \frac{1}{m \cdot n} \sum_{k=1}^{m} \sum_{l=1}^{n} f(k, l)$$ [Equation 1]

where (k,l) is an image in the vicinity of (i,j). By expressing the overall average density of the image f as <f>, an after-correction image h can be obtained as follows.

$$h(i, j) = f(i, j) \cdot \frac{<f>}{g(i, j)}$$ [Equation 2]

By using D as the maximum diameter of the knot to be detected as an indication, and by limiting D to around m=n=2D, all color irregularities in excess thereof can be removed (smoothed) while retaining the knot portion. In addition, when m and n are significantly large, representative points (for instance, lattice points) may be used for the calculation instead of using all points within the neighborhood.

Since the obtained smoothed image h is always normalized on <f>, knot candidates can be easily determined by performing binarization using an appropriate threshold (for instance, 50% of <f>). The use of such methods allows practical and speedy determination of knot candidates.

Figure 8:
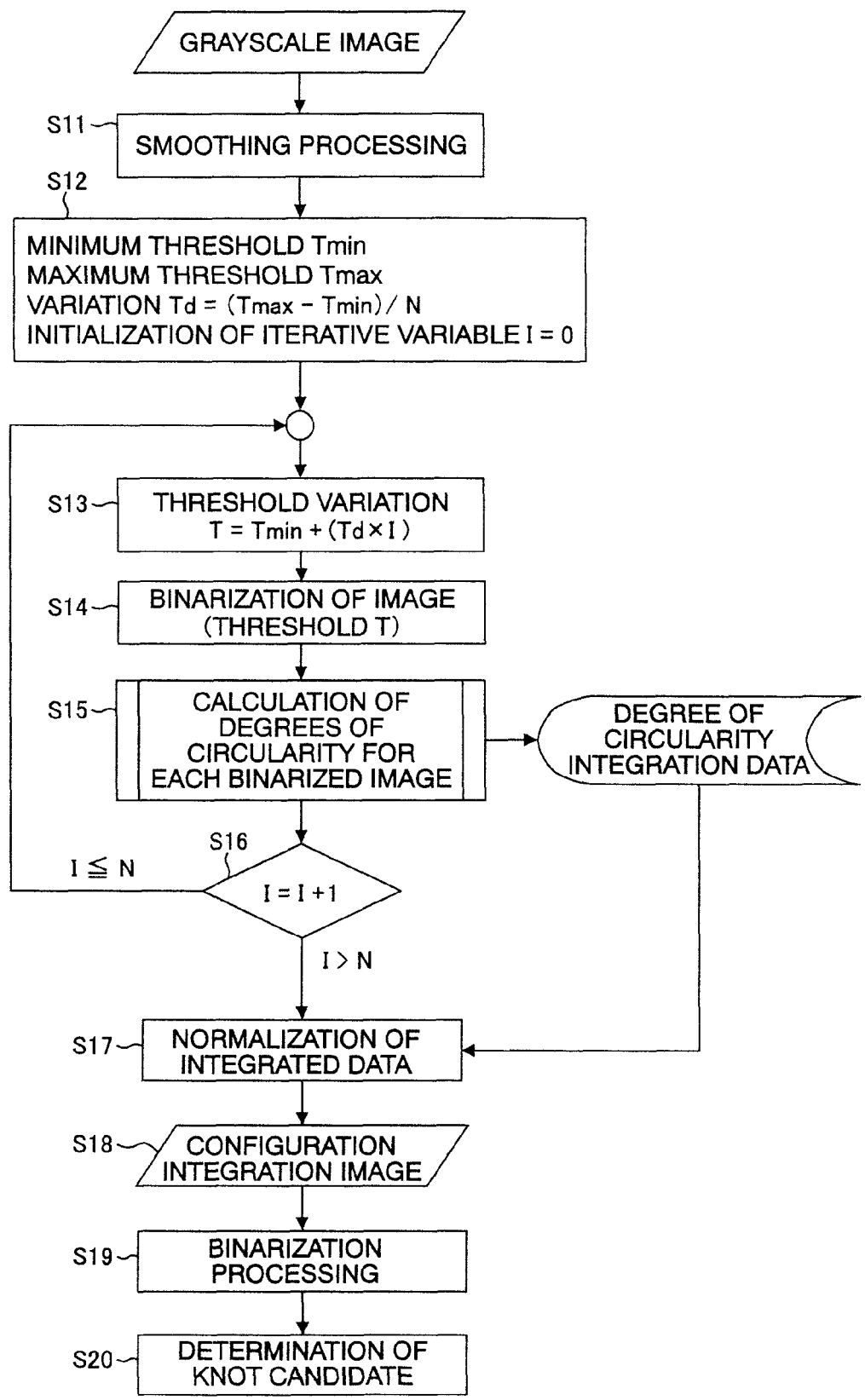
FIG. 8 is a flowchart of knot searching processing involving smoothing processing according to the present invention.

FIG. 8 is a flowchart of knot searching processing involving smoothing processing.

In FIG. 8, the image processing apparatus 1 performs smoothing processing of a received grayscale image to create a smoothed image (image h) in step S11, and proceeds to step S12.

In the following steps S12 to S20, the same processing as shown in FIG. 3 (represented by steps S1 to S9) is performed on the smoothed image to determine a knot candidate. By performing smoothing processing in this manner, the amount of information unrelated to knots can be reduced, thereby enabling quick determination of knot candidates.

(4) Description of Determination of Knot Configuration

The processing for knot configuration determination involves obtaining an optimal frame from density changes around a knot position in order to more accurately obtain a knot frame. To be more specific, the processing obtains optimal threshold values and performs binarization for each knot. As a result, optimal configurations and sizes are respectively obtained for each knot candidate. In this processing, for each concatenated pixel element (hereinafter referred to as "block") (see FIG. 7) obtained by the above binarization, a threshold that produces an optimal configuration is derived from an configuration integration image and a differential image for a region that is larger than each knot candidate block, such as a quadruple-size extended region. Since this is respectively performed for each partial space, respective knot configurations can be accurately determined.

In the following description, the number of pixels of a binarized block will be referred to as block size (or size). In addition, size stability (S) is defined as the variation in size when changing a threshold (the block size variation of a knot portion when changing a threshold remains small up to a certain threshold. In other words, knot portions have a high stability. However, once grains appear as a result of changing a threshold, block size variations become significant. This allows removal of blurred patterns such as stains).

Figure 9:
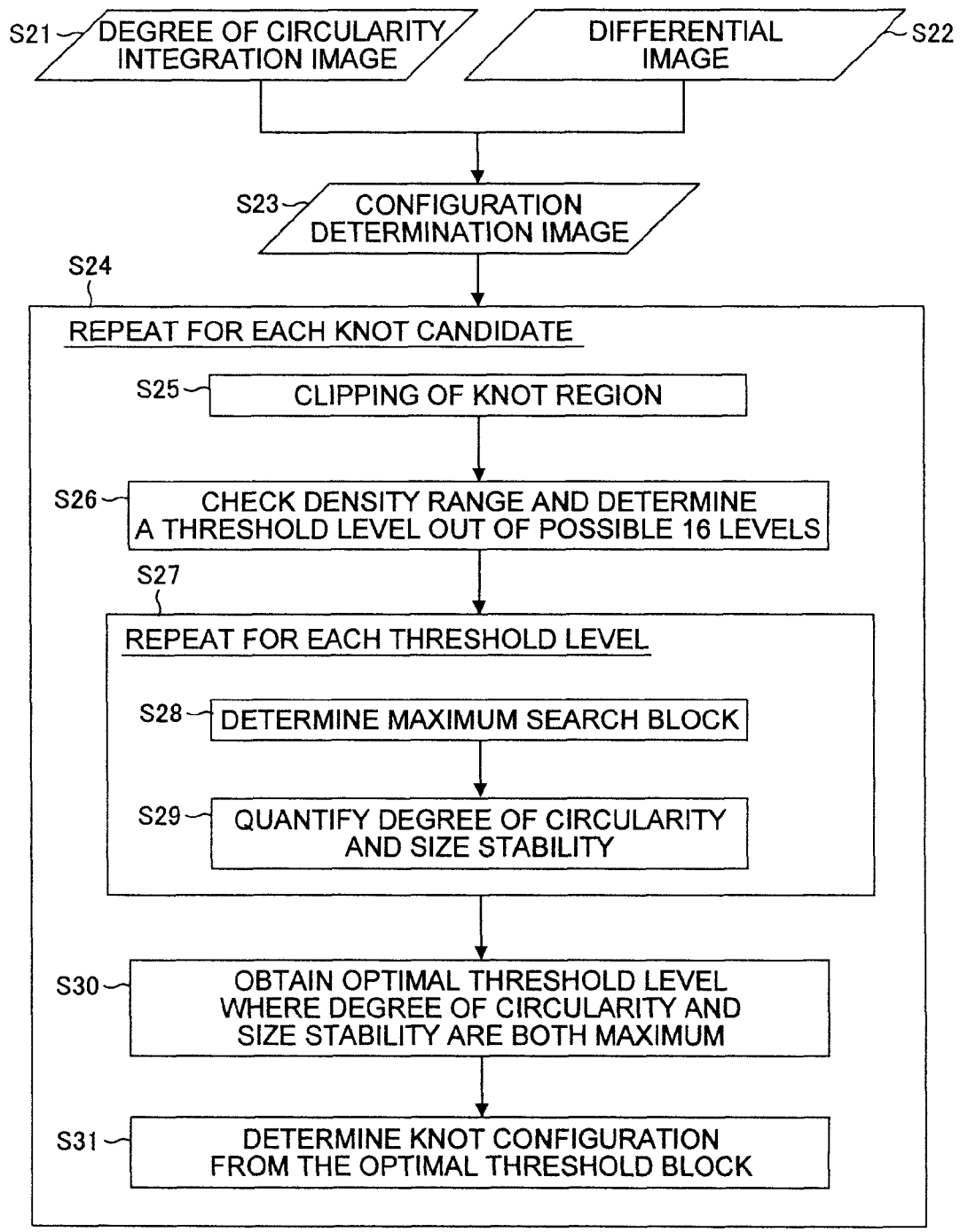
FIG. 9 is a flowchart of processing of knot configuration determination according to the present invention.

FIG. 9 is a flowchart of processing of knot configuration determination. The following description will be provided along with the steps S21 to S31 shown in FIG. 9.

S21: The image processing apparatus 1 loads a degree of circularity integration image (refer to S7) of a veneer, and proceeds to step S23.

S22: The image processing apparatus 1 creates a differential image of the veneer to highlight its edge portions, and proceeds to step S23.

S23: The image processing apparatus 1 creates a configuration determination image by adding the degree of circularity integration image and the differential image (in case of subtraction, the sign is changed to negative and then added), and proceeds to step S24.

S24: The image processing apparatus 1 repeats the following steps S25 to S31 for each knot candidate.

S25: The image processing apparatus 1 clips a knot candidate from a grayscale image of the entire veneer and proceeds to step S26. Here, the clipping is performed on a quadruple-size extended region of the knot candidate block (refer to FIG. 7).

S26: The image processing apparatus 1 studies the density range of the configuration determination image to determine a threshold level out of a possible sixteen levels, and proceeds to step S27.

S27: The image processing apparatus 1 repeats the following steps S28 and S29 for each threshold level (in this case, sixteen times).

S28: The image processing apparatus 1 determines a maximum searching block, and proceeds to step S29.

S29: The image processing apparatus 1 digitizes the degree of circularity and the size stability, and proceeds to step S30.

S30: The image processing apparatus 1 calculates an optimal threshold level at which the degree of circularity and the size stability are both maximum (a threshold level where changing the threshold does not result in significant size variation), and proceeds to step S31.

S31: Based on the optimal threshold level block, the image processing apparatus 1 determines the knot configuration.

Figure 10A:
FIGS. 10A, 10B, 10C and 10D are explanatory diagrams using an image of knot configuration determination according to the present invention.
Figure 10B:
Figure 10C:
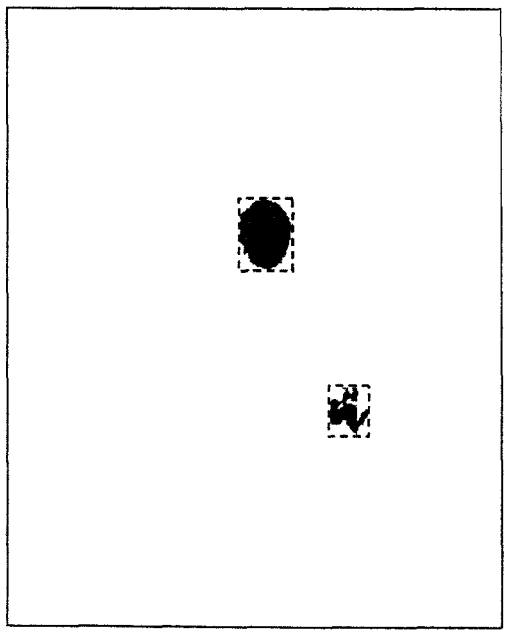
Figure 10D:
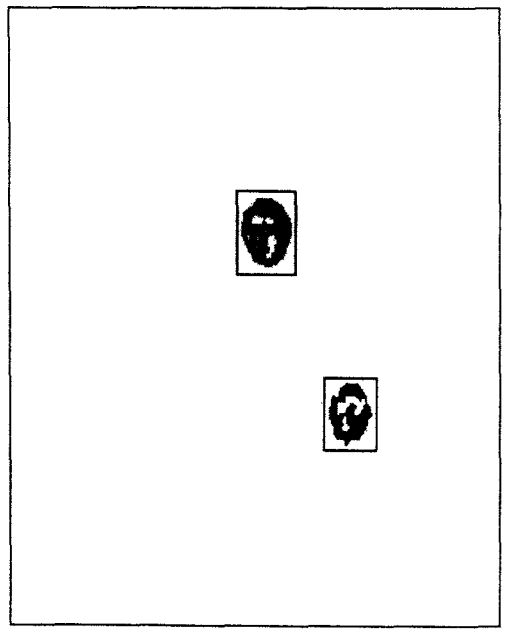

FIGS. 10A, 10B, 10C, and 10D are explanatory diagrams using an image of knot configuration determination. FIG. 10A illustrates a degree of circularity integration image, FIG. 10B illustrates a differential image, FIG. 10C illustrates a knot candidate obtained by the degree of circularity integration, and FIG. 10D illustrates an image binarized by an optimal threshold.

FIG. 10A is the degree of circularity integration image explained in FIG. 7A. While the sizes of the knots are virtually obtained with this degree of circularity integration image, in order to further increase accuracy, the linear differential image of FIG. 10B is superimposed over a density image of the degree of circularity integration image. As a result, the edges of the knots are highlighted.

FIG. 10D shows the result of obtaining optimal thresholds for each knot from the superimposed image. In this image, the lower knot can be more clearly judged as compared to the image of knot candidates obtained by degree of circularity integration shown in FIG. 10C. In addition, knot frames can be newly obtained.

Moreover, with optimum thresholds, if a judgment value is to be represented by a function having the degree of circularity, size stability, threshold depth and block size of the knot candidate block, the function can be determined so that the threshold with the maximum judgment value is the maximum threshold (details may have to be changed for different materials).

(5) Description of Judgment of Live and Dead Knots

Dead knots are knots containing bark portions. Dead knots are considered inferior knots, since the knots are likely to fall out and leave holes. In addition, the bark portions of dead knots are carbonized during a drying process using a dryer, resulting in higher color deviation values. When a region surrounding a knot block obtained earlier has a high proportion of color deviation value (in this case, a color image is used), the knot can be judged to be a dead knot.

Figure 11:
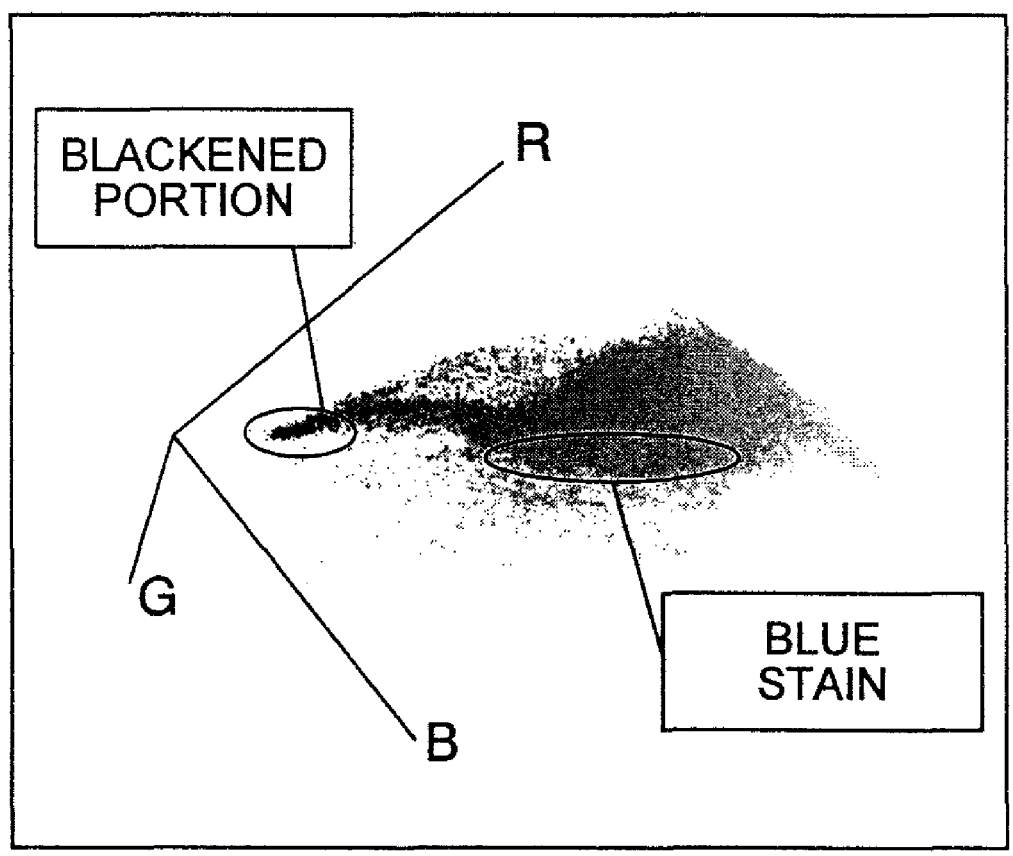
FIG. 11 is an explanatory diagram of a three-dimensional color distribution according to the present invention.
Figure 12:
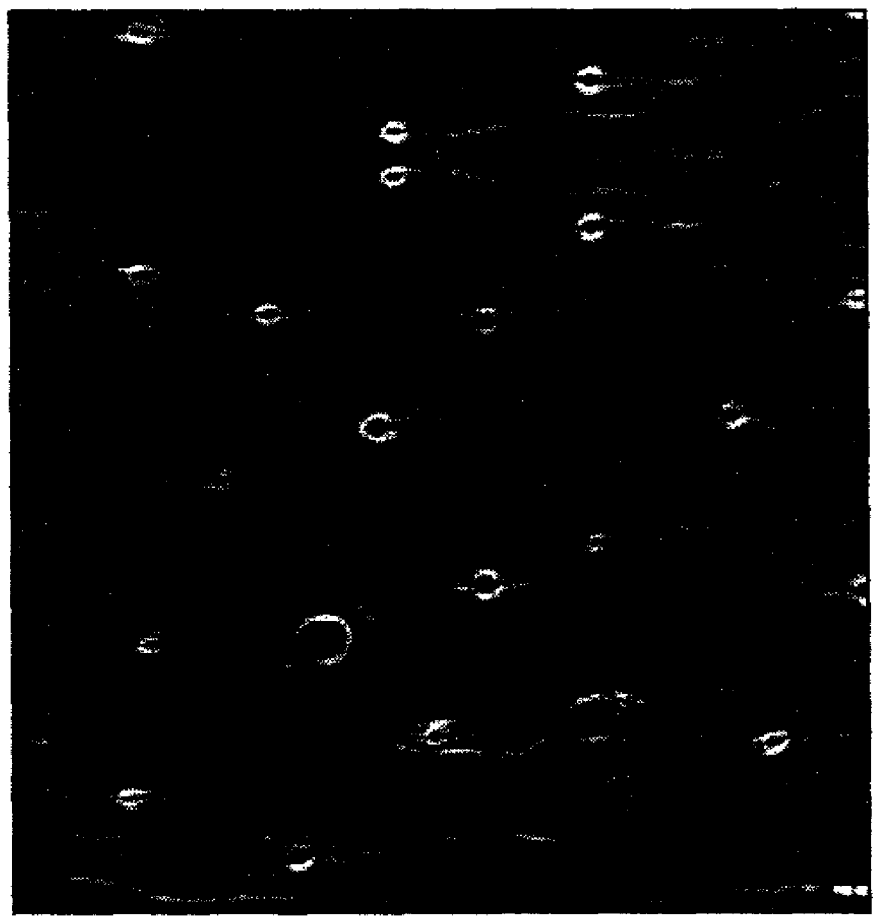
FIG. 12 is an explanatory diagram of a color deviation image according to the present invention.

FIG. 11 is an explanatory diagram of a three-dimensional color distribution. FIG. 11 shows the three-dimensional color distribution (RGB) of a region surrounding a knot block. Blackened portions and blue stains (burns, externally introduced mold or the like) are the regions marked by ellipses. Such regions produce distributions that are biased from a standard distribution of the original color of a veneer. It is likely that such portions indicate some kind of defect. FIG. 12 is an image created from only the blackened portions of FIG. 11.

FIG. 12 is an explanatory diagram of a color deviation image. In FIG. 12, the color deviation image is an imaging of the spatial distances from a central color (the average value of RGB) within the normalized color space of each pixel. In this case, imaging is performed on the blackened portion of FIG. 11. In actual processing, with 0 (black) as the overall mean hue value, the image processing apparatus 1 multiplies the deviation values of each pixel by an appropriate coefficient (to further highlight the black portion) to perform imaging. This allows detection of discolored portions due to reasons other than natural wood, such as burns. Dead knots can be detected, since the bark portions are carbonized during a drying process using a dryer, resulting in higher color deviation values. The resulting image is as shown in FIG. 12.

(6) Description of Program Installation

The image processing apparatus (image processing means) 1, the sorter control apparatus (sorter control means) 2, the camera PC1 to PC3, the group of image processing computers 13, the calculation server PC 14, the display apparatus (display means) 15 and the like are all configurable as programs executed by a main control section (CPU) and stored in a main storage. The programs are to be installed in a computer to make it execute predetermined processing. The computer is composed of hardware such as a main control section, a main storage, a file device, an output device such as a display device, and an input device.

The programs according to the present invention are installed onto this computer. Installation is performed by storing in advance the programs onto a portable storage (recording) media such as a floppy or a magnetic optical disk and the like, and installing the storage media into a file device provided in the computer either via a drive device provided on the computer to enable access by storage media or via a network such as a LAN.

In this manner, accurate detection of knots in wood, as well as accurate determination of the configurations of knots in wood may be achieved. In addition, an apparatus for searching knots in wood that is capable of accurately detecting dead knots may be easily provided.

What is claimed is:

1. A method executed by a programmed processor for searching knots in wood, the method comprising:

photographing a piece of wood by a photographing unit;

performing a first calculation comprising calculating degrees of circularity of each figure in the photographed images of the piece of wood and setting at least one figure comprising a circularity corresponding to a knot candidate;

clipping a partial image including said knot candidate from said at least one figure;

varying threshold levels of gray value for said clipped partial image such that an image is obtained at each of said threshold levels, said image including said knot candidate;

performing a second calculation, said second calculation comprising calculating a degree of circularity and stability of said knot candidate at each of said threshold levels;

identifying one of said images from said plurality of images comprising a selected threshold level, said selected threshold level corresponding to a level at which said circularity and said size stability of said knot candidate is a maximum value with respect to said circularity and said size stability values of said knot candidate in said other images;

determining a configuration of said knot candidate at said selected threshold level;

detecting said knot candidate as a knot when said degree of said circularity of said knot candidate is greater than a predetermined circularity degree at said selected threshold level.

2. The method according to claim 1, wherein:

said second calculation sets a value table to hold a value associated with each pixel of said photographed image, wherein said second calculation comprises calculating a coefficient corresponding to said degree of circularity of said figure of said knot candidate for each image of each of said threshold levels and said second calculation comprises accumulating said calculated coefficients to values of said value table associated with said pixels forming said figure; and said determining a configuration step includes specifying specific values of said value table that exceed a predetermined value and determining, as said figure of said knot candidate, a figure generated with said pixels associated with said specific values of said value table after accumulating said coefficients in said second calculation.

3. The method according to claim 1, further comprising:
determining a portion with pixels clipped at a predetermined threshold from a color space as a blackened portion based on the pixels of the partial image; and
determining said knot candidate as a dead knot, said knot candidate having a high proportion of the number of pixels of the blackened portion to the number of pixels thereof.

4. The method according to claim 1, further comprising
performing smoothing on color shadings that are larger than knots on the photographed image of the piece of wood, and
wherein the calculating calculates degrees of circularity from the smoothed images and deems a figure with a high degree of circularity to be the knot candidate.

5. An apparatus for searching knots in wood, comprising:
a photographing unit for photographing pieces of wood;
an image processing unit, said image processing unit being programmed for:
performing a first calculation comprising calculating degrees of circularity of each figure in the photographed images of the piece of wood and setting at least one figure comprising a circularity corresponding to a knot candidate;
clipping a partial image including said knot candidate from said at least one figure;
varying threshold levels of gray value for said clipped partial image such that an image is obtained at each of said threshold levels, said image including said knot candidate;
performing a second calculation, said second calculation comprising calculating a degree of circularity and stability of said knot candidate at each of said threshold levels;
selecting one of said images from said plurality of images, said one of said images comprising a selected threshold level, said selected threshold level corresponding to a level at which said circularity and said size stability of said knot candidate is a maximum value with respect to said circularity and said size stability values of said knot candidate in said other images;
determining a configuration of said knot candidate at said selected threshold level;
detecting said knot candidate as a knot when said degree of said circularity of said knot candidate is greater than a predetermined circularity degree at said selected threshold level.

6. The apparatus according to claim 5, wherein:
said second calculation sets a value table to hold a value associated with each pixel of said photographed image, wherein said second calculation comprises calculating a coefficient corresponding to said degree of circularity of said figure of said knot candidate for each image of each of said threshold levels and said second calculation comprises accumulating said calculated coefficients to values of said value table associated with said pixels forming said figure; and
said determining a configuration step includes specifying specific values of said value table that exceed a predetermined value and determining, as said figure of said knot candidate, a figure generated with said pixels associated with said specific values of said value table after accumulating said coefficients in said second calculation.

7. The apparatus according to claim 5, wherein the image processing unit:
determines a portion with pixels clipped at a predetermined threshold from a color space as a blackened portion based on the pixels of said partial image; and
determines, as dead knots, black portions with a high proportion of a number of pixels of the blackened portion to the number of pixels of the knot candidate.

8. The apparatus according to claim 5, further comprising
a smoothing unit for performing smoothing on color shadings that are larger than knots on the photographed images of the piece of wood and
wherein the image processing unit calculates degrees of circularity from the smoothed images and deems a figure with a high degrees of circularity to be the knot candidate.

9. A non-transitory computer-readable storage medium storing a program for enabling a computer to function as an image processing apparatus comprising:
a unit programmed for:
performing a first calculation, said first calculation comprising calculating degrees of circularity of each figure in the photographed images of the piece of wood and setting at least one figure comprising a circularity corresponding to a knot candidate;
clipping a partial image including said knot candidate from said at least one figure;
varying threshold levels of gray value for said clipped partial image such that an image is obtained at each of said threshold levels, said image including said knot candidate;
performing a second calculation, said second calculation comprising calculating a degree of circularity and stability of said knot candidate at each of said threshold levels;
identifying one of said images from said plurality of images, said one of said images comprising a selected threshold level, said selected threshold level corresponding to a level at which said circularity and said size stability of said knot candidate is a maximum value with respect to said circularity and said size stability values of said knot candidate in said other images;
determining a configuration of said knot candidate at said selected threshold level;
detecting said knot candidate as a knot when said degree of said circularity of said knot candidate is greater than a predetermined circularity degree at said selected threshold level.

10. The non-transitory computer readable storage program according to claim 9, wherein:
said second calculation sets a value table to hold a value associated with each pixel of said photographed image, wherein said second calculation comprises calculating a coefficient corresponding to said degree of circularity of said figure of said knot candidate for each image of each of said threshold levels and said second calculation comprises accumulating said calculated coefficients to values of said value table associated with said pixels forming said figure; and
said determining a configuration step includes specifying specific values of said value table that exceed a predetermined value and determining, as said figure of said knot candidate, a figure generated with said pixels associated with said specific values of said value table after accumulating said coefficients in said second calculation.

11. The non-transitory computer-readable storage medium according to claim 9, wherein the unit determines a portion with pixels clipped at a predetermined threshold from a color space as a blackened portion based on the pixels of the partial image; and determines, as dead knots, black portions with a high proportion of a number of pixels of the blackened portion to the number of pixels of the knot candidate.

12. The non-transitory computer readable storage program according to claim 9, further comprising:
   a unit for performing smoothing on color shadings that are larger than knots on the photographed images of the piece of wood and
   wherein the unit for calculating calculates degrees of circularity from the smoothed images and deems a figure with a high degree of circularity to be the knot candidate.

13. The method according to claim 3, wherein said step of determining said portion of pixels as a blackened portion includes calculating a deviation of each of said pixels of said partial images in said color space and determining said blackened portion based on a portion with pixels deviating from a predetermined threshold in said color space.

14. The method according to claim 1, further comprising the steps of:
   providing a distributing means for sorting one or more pieces of wood;
   sorting at least one said piece of wood based on said degree of circularity of said knot candidate with said distributing means.

15. The apparatus according to claim 5, further comprising:
   a grading and distributing apparatus, said grading and distributing apparatus sorting at least one said piece of wood based on said degree of circularity of said knot candidate with said distributing means.

16. The non-transitory computer-readable storage medium according to claim 9, wherein at least one said piece of wood is sorted based on degree of circularity of said knot candidate.

* * * * *